(12) United States Patent
Li et al.

(10) Patent No.: US 8,937,053 B2
(45) Date of Patent: Jan. 20, 2015

(54) PROCESS FOR THE PREPARATION OF PRASUGREL AND SEVERAL NOVEL CRYSTALLINE FORMS OF PRASUGREL HYDROCHLORIDE

(75) Inventors: Lijun Li, Dongguan (CN); Hailong Wang, Dongguan (CN); Zhongqing Wang, Dongguan (CN)

(73) Assignees: Sunshine Lake Pharma Co., Ltd., Dongguan, Guangdong (CN); Yichang Changjiang Pharmaceutical Co., Ltd., Yidu, Hubei (CN)

( * ) Notice: Subject to any disclaimer, the term of this patent is extended or adjusted under 35 U.S.C. 154(b) by 0 days.

(21) Appl. No.: 14/123,109

(22) PCT Filed: Jun. 21, 2012

(86) PCT No.: PCT/CN2012/077320
§ 371 (c)(1),
(2), (4) Date: Jan. 22, 2014

(87) PCT Pub. No.: WO2012/175031
PCT Pub. Date: Dec. 27, 2012

(65) Prior Publication Data
US 2014/0155351 A1    Jun. 5, 2014

(30) Foreign Application Priority Data

Jun. 22, 2011  (CN) .......................... 2011 1 0169901

(51) Int. Cl.
| | | |
|---|---|---|
| *C07D 491/02* | (2006.01) | |
| *A61K 31/695* | (2006.01) | |
| *C07F 7/18* | (2006.01) | |
| *C07D 495/04* | (2006.01) | |

(52) U.S. Cl.
CPC .............. *C07F 7/188* (2013.01); *C07D 495/04* (2013.01); *C07F 7/1844* (2013.01)
USPC ........................................... 514/63; 546/116

(58) Field of Classification Search
None
See application file for complete search history.

(56) References Cited

U.S. PATENT DOCUMENTS

| | | | |
|---|---|---|---|
| 5,874,581 A | 2/1999 | Ataka et al. | |
| 6,693,115 B2 | 2/2004 | Asai et al. | |
| 8,193,358 B2 | 6/2012 | Hagihara et al. | |
| 2010/0094013 A1 | 4/2010 | Miyata et al. | |
| 2010/0261908 A1 | 10/2010 | Padi et al. | |

FOREIGN PATENT DOCUMENTS

| | | |
|---|---|---|
| CN | 101245072 | 8/2008 |
| CN | 101402642 | 4/2009 |
| CN | 101402643 | 4/2009 |
| CN | 102212071 | 10/2011 |
| WO | WO 2010/070677 A2 | 6/2010 |
| WO | WO 2011/124124 A1 | 10/2011 |
| WO | WO 2012/001486 A1 | 1/2012 |

*Primary Examiner* — Heidi Reese
(74) *Attorney, Agent, or Firm* — Kam W. Law; Squire Patton Boggs

(57) ABSTRACT

Disclosed herein are a process or method for the preparation of prasugrel and several novel crystalline forms of prasugrel hydrochloride. The process comprises preparation of prasugrel by acetylation in solvents which have low boiling point and/or low toxicity, and the process not only avoids using solvents which have high boiling point and/or high toxicity such as toluene, acetonitrile and so on, but also resolves the problem about thermal instability of prasugrel, and the loss of prasugrel is reduced, as well as the yield is raised. The yield of prasugrel is higher than 85% and the purity is higher than 99.5%. The process can prepare prasugrel and its pharmaceutically acceptable salts. The novel crystalline forms of prasugrel hydrochloride are crystalline form H1, H2 and H3, and their performance in oral absorbability, activating metabolism and inhibiting platelet aggregation is excellent. They have a low toxicity and good thermal stability, and are applicable to the preparation of a drug for preventing or treating diseases caused by thrombosis or embolism.

12 Claims, 6 Drawing Sheets

PROCESS FOR THE PREPARATION OF PRASUGREL AND SEVERAL NOVEL CRYSTALLINE FORMS OF PRASUGREL HYDROCHLORIDE

CROSS-REFERENCE TO RELATED APPLICATIONS

This is a U.S. national stage application of the International Patent Application No. PCT/CN2012/077320, filed Jun. 21, 2012, which claims priority to Chinese Patent Application No. 201110169901.X, filed Jun. 22, 2011, both of which are incorporated herein by reference in their entirety.

FIELD OF THE INVENTION

The present invention relates to the field of pharmaceutical chemistry. More particularly, the invention relates to methods for preparing prasugrel and several novel crystalline forms of prasugrel hydrochloride.

BACKGROUND OF THE INVENTION

Prasugrel, also known as 2-[2-(acetyloxy)-6,7-dihydrothieno[3,2-c]-pyridin-5(4H)-yl]-1-cyclopropyl-2-(2-fluorophenyl)ethanone, is a thienopyridine drug developed by Sankyo (Daiichi Sankyo) and Eli Lilly, and approved by EU on 23 Feb. 2009 as a platelet aggregation inhibitor. Prasugrel has Formula (I) as shown below:

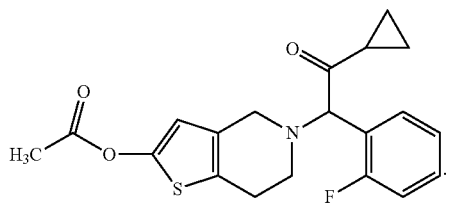

(I)

Prasugrel and pharmaceutical acceptable salts thereof are platelet aggregation inhibitors from the thienopyridine class of ADP (Adenosine diphosphate) receptor for prophylaxis and therapy of thrombosis with improved oral bioavailability and rapid onset. However, highly pure prasugrel and pharmaceutical salts thereof needed to be provided when used as a medicine.

There are many methods for preparing prasugrel. A common method used to prepare prasugrel is by condensing halogen substituted cyclopropyl-2-fluorobenzyl ketone with 5,6,7,7a-tetrahydrothieno[3,2-c]pyridine-2(4H)-one to obtain a condensation product. The condensation product is then mixed with an acetylation agent in toluene, DMF, etc. to produce prasugrel (I). The above method is described in PCT publication WO 96/11203 as shown in the following scheme:

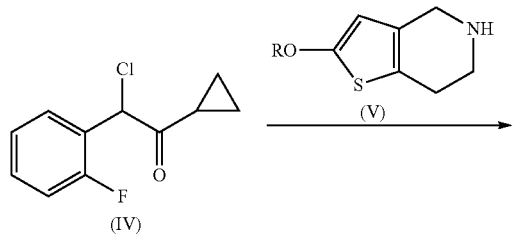

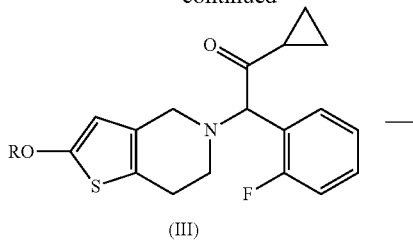

(III)

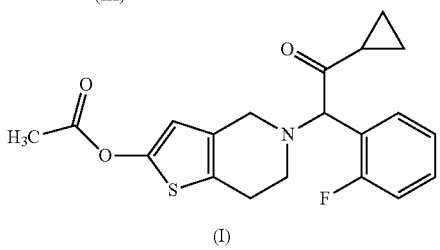

(I)

wherein R in Formula (III) and (V) is a hydroxy protecting group.

However, there are some disadvantages in the aforementioned preparation methods, such as the acetylation reaction is carried out in toxic or high boiling solvents, such as acetonitrile, dimethylformamide or toluene, which are harmful to environment as well as health. Furthermore, removing high boiling solvents such as dimethylformamide or toluene requires a high temperature. However, the prasugrel free base and its intermediate thereof are thermally instable, and prone to degradation at the high temperature. Therefore, the purity of the final product is low, which makes it unsuitable for use as an active pharmaceutical ingredient (API). Moreover, recycling the high boiling solvents is energy consuming and thus costly.

PCT Patent Publication No. WO 96/11203, Japanese Patent Publication No. 2002/145883 and U.S. Pat. No. 6,693,115 describe a method for preparing prasugrel hydrochloride having formula (II) by mixing hydrochloric acid with prasugrel free base of Formula (I):

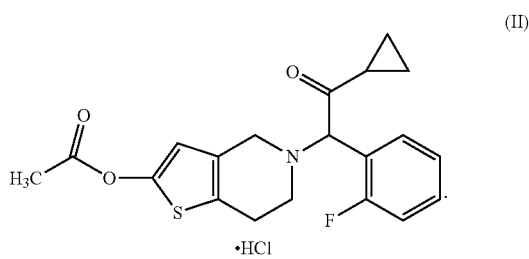 [SMILES: CC(=O)Oc1cc2c(s1)CCN(C(C(=O)C1CC1)c1ccccc1F)C2 ; Cl]

(II)

However, prasugrel hydrochloride prepared by the aforementioned method exists in mixture of unknown polymorphic forms, which may have significant differences from each other in appearances, solubilities, melting points, dissolution rates, bioavailabilities, stability, efficacy and the like. Therefore, there is a need for considering the issue of polymorph in developing a pharmaceutical product.

So far, it is known that prasugrel hydrochloride exists in several polymorphic forms. Crystalline forms A, B1 and B2 of prasugrel hydrochloride was first disclosed in PCT Patent Publication No. WO 2002/004461. PCT Patent Publication No. WO 2009/062044 has disclosed crystalline forms C, D and E as well as amorphous prasugrel hydrochloride. PCT Patent Publication No. WO 2010/070677 has disclosed crystalline forms G1 and G2.

SUMMARY OF THE INVENTION

In one aspect, provided herein are methods for preparing prasugrel comprising acetylating a compound of formula (IE):

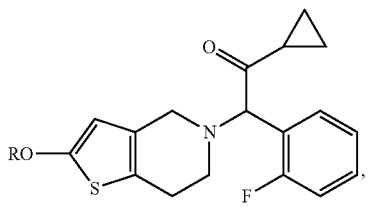

(III)

with an acetylating agent in a solvent and in the presence of a base, wherein the solvent has a boiling point of less than 80° C. and an oral median lethal dose ($LD_{50}$) higher than 2500 mg/Kg, wherein the compound of Formula (III) is prepared by the steps of condensing a compound of Formula (IV) with a compound of Formula (V) or a salt thereof to form a product, and purifying the product;

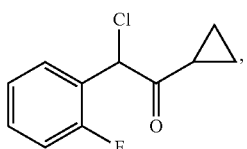

(IV)

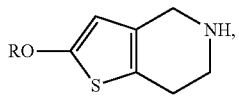

(V)

wherein the purifying step is recrystallizing the compound of Formula (III) with a mixture of acetone and water, and wherein R is a hydroxy protecting group selected from p-toluenesulfonyl, methanesulfonyl, or a silyl having the following formula:

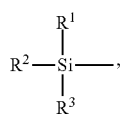

wherein each of R', $R^2$ and $R^3$ is independently $C_1$-$C_{10}$ alkyl.

In certain embodiments, the alkyl is $C_1$-$C_6$ alkyl or methyl. In some embodiments, the solvent is acetone, methyl ethyl ketone or a combination thereof. In certain embodiments, the acetylating agent is acetyl chloride, acetyl bromide, acetic anhydride or a combination thereof. In some embodiments, the base is a tertiary amine, a secondary amine, diethylamine, triethylamine or a combination thereof. In certain embodiments, the acetylating reaction is carried out in the presence of an acetylation catalyst, wherein the acetylation catalyst is a 4-dialkylaminopyridine. In some embodiments, the acetone and water is from 0.5:1 to 3:1, or from 0.8:1 to 2.5:1, or from 0.9:1 to 2.1:1, or from 0.9:1 to 1.1:1, or from 1.9:1 to 2.1:1, or from 1:1, or 2:1.

In another aspect, provided herein is a crystalline form of prasugrel hydrochloride, wherein the crystalline form is form H1 or form H3, wherein a) form H1 has an X-ray powder diffraction pattern comprising peaks expressed in degrees 2η at 14.02, 15.92, 18.56, 23.66, 24.46, 25.92 and 26.62±0.3 degrees; or b) form H3 has an X-ray powder diffraction pattern comprising peaks expressed in degrees 2η at 13.38, 13.78, 14.34, 16.06, 21.48, 22.06 and 25.66±0.3 degrees.

In some embodiments, the crystalline form disclosed herein is form H1 having an X-ray powder diffraction pattern comprising peaks expressed in degrees 2θ at 8.02, 8.46, 10.28, 12.34, 12.88, 13.38, 14.02, 14.36, 15.92, 17.36, 18.56, 18.86, 20.54, 22.04, 23.66, 24.46, 25.92, 26.62, 28.3, 29.46 and 30.7±0.3 degrees.

In some embodiments, the crystalline form is form H3 having an X-ray powder diffraction pattern comprising peaks expressed in degrees 2θ at 7.98, 12.86, 13.38, 13.78, 14.34, 16.06, 17.12, 18.66, 20.52, 21.48, 22.06, 23.70, 25.66, 27.14, 27.64, 28.32 and 29.44±0.3 degrees.

In another aspect, provided herein is a method for preparing crystalline form of prasugrel hydrochloride comprising dissolving prasugrel hydrochloride in a good solvent to form a solution; and forming crystals by adding the solution slowly into an anti-solvent, wherein the good solvent is an alcohol solvent, a carboxylic acid solvent or a combination thereof, and the anti-solvent is an ether solvent, an aromatic solvent, an ester solvent or a combination thereof.

In some embodiments, the good solvent is an alcohol solvent, or methanol, ethanol, n-propanol, isopropanol or n-butanol or a combination thereof, and the anti-solvent is an ester solvent or ethyl acetate. In certain embodiments, the good solvent is acetic acid, and the anti-solvent is an ester solvent or ethyl acetate. In some embodiments, the good solvent is acetic acid, and the anti-solvent is an aromatic hydrocarbon solvent or toluene. In certain embodiments, the good solvent is acetic acid, and the anti-solvent is an ether solvent or methyl ten-butyl ether.

In another aspect, provided herein is a method for preventing or treating diseases caused by thrombosis or embolism in a patient by administering to the patient a pharmaceutically effective amount of the crystalline form of prasugrel hydrochloride.

DETAILED DESCRIPTION OF THE INVENTION

Figure 1:
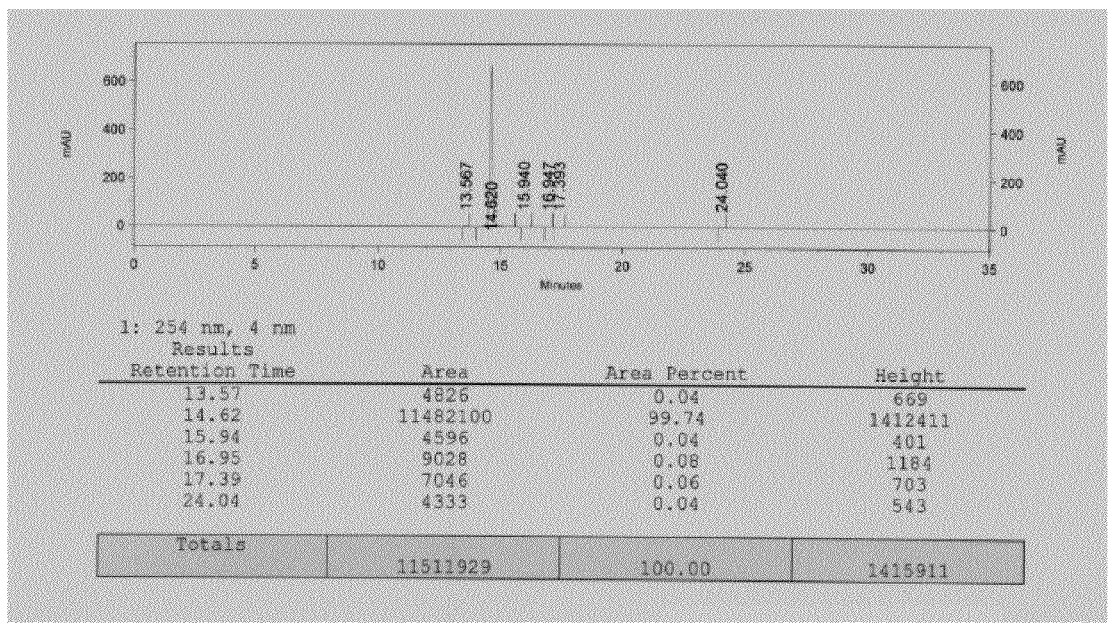
FIG. 1 depicts the High Performance Liquid Chromatography (HPLC) spectrum of prasugrel prepared according to example 3.
Figure 2:
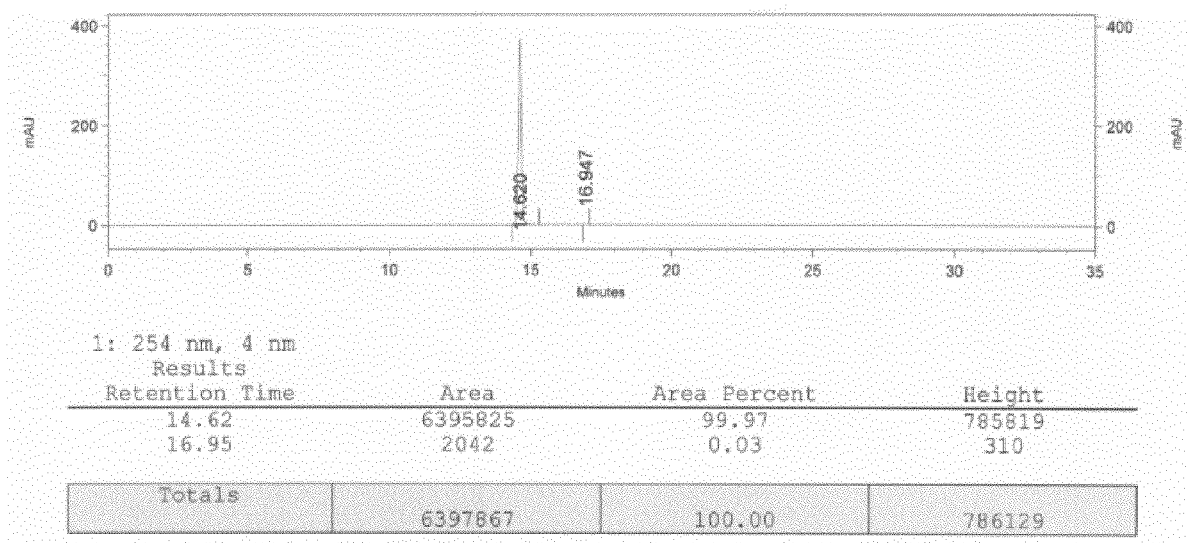
FIG. 2 depicts the HPLC spectrum of prasugrel prepared according to example 5.

Provided herein is a method for preparing prasugrel, wherein the prasugrel made by the method is highly pure. Also provided herein are several novel crystalline forms of prasugrel hydrochloride. Also provided herein are methods for preparing the novel crystalline forms of prasugrel hydrochloride disclosed herein. The novel crystalline forms of prasugrel hydrochloride are substantially pure and have low toxicity, good thermal stability, good solubility and high bioavailability.

The term "low boiling point" refers to the boiling point of a solvent is less than 100° C., less than 90° C., less than 80° C., less than 70° C. or less than 60° C. The term "low toxicity" refers to solvent regarded as less toxic and of lower risk to human health. Available data indicate that they are less toxic in acute or short-term studies and negative in genotoxicity. There are no long-term toxicity or carcinogenicity studies for most of these solvent. Some of these low toxicity solvents can be found in Class 3 of the Chinese Pharmacopoeia.

In the following description, all numbers disclosed herein are approximate values, regardless whether the word "about" is used in connection therewith. The value of each number may differ by 1%, 2%, 5%, 7%, 8%, 10%, 15% or 20%. Therefore, whenever a number having a value N is disclosed, any number having the value N+/−1%, N+/−2%, N+/−3%, N+/−5%, N+/−7%, N+/−8%, N+/−10%, N+/−15% or 20 N+/−20% is specifically disclosed, wherein "+/−" refers to plus or minus. Whenever a numerical range with a lower limit, $R_L$, and an upper limit, $R_U$, is disclosed, any number falling within the range is specifically disclosed. In particular, the following numbers within the range are specifically disclosed: $R=R_L+k*(R_U-R_L)$, wherein k is a variable ranging from 1% to 100% with a 1% increment, i.e., k is 1%, 2%, 3%, 4%, 5%, . . . , 50%, 51%, 52%, . . . , 95%, 96%, 97%, 98%, 99%, or 100%. Moreover, any numerical range defined by two R numbers as defined above is also specifically disclosed.

Some non-limiting embodiments of the present invention are disclosed as follows.

In one aspect, disclosed herein is a method for preparing prasugrel of Formula (I), comprising acetylating a compound of Formula (III) with an acetylating agent in a solvent and in the presence of a base, wherein the solvent has a low boiling point and/or a low toxicity,

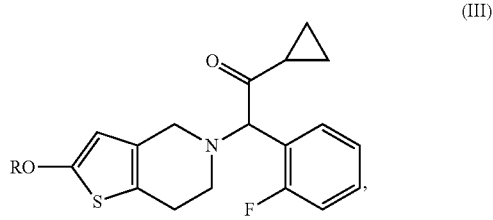

(III)

wherein R is a hydroxy protecting group.

Any hydroxy protecting group that may protect a hydroxy group can be used herein. In certain embodiments, the hydroxy protecting group is a leaving group, such as Cl, Br, I and sulfonyl. In some embodiments, the hydroxy protecting group is p-toluenesulfonyl, methanesulfonyl, or silyl having the following formula:

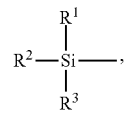

wherein each of $R^1$, $R^2$ and $R^3$ independently is an alkyl group having 1 to 10 carbon atoms, wherein the alky group is straight or branched. Some non-limiting examples of the alkyl group include methyl, ethyl, propyl (including all structural isomers thereof), butyl (including all structural isomers thereof), a pentyl group (including all structural isomers thereof), hexyl (including all structural isomers thereof), heptyl (including all structural isomers thereof), octyl (including all structural isomers thereof), nonyl (including all structural isomers thereof), or decyl (all structural isomers thereof). In some embodiments, each of $R^1$, $R^2$ and $R^3$ is independently $C_1$-$C_5$ alkyl. In some embodiments, the hydroxy protecting group is trimethylsilyl, triethylsilyl, tri-propyl silyl, triisopropyl silyl, tert-butyldimethylsilyl, tert-butyldiphenylsilyl or a combination thereof. In some embodiments, the hydroxy protecting group is tert-butyl dimethyl silyl.

Prasugrel free base and its intermediate are thermally instable, and prone to degradation under high reaction temperature. The method for preparing prasugrel disclosed herein comprises dissolving the compound of Formula (III) in a solvent having a low boiling point and/or a low toxicity, then acetylating the compound in the presence of a base to obtain prasugrel. The method disclosed herein avoids the thermal instability problem of prasugrel and its intermediate at high temperatures, and thus reduces the loss of prasugrel. As a result, the yield of prasugrel is improved.

The solvents with different toxicity used in the preparation method may pose different health risks to human and affect the quality of medicine differently. The toxicity effect of a solvent includes teratogenicity, carcinogenicity and lethal. According to the United States Pharmacopoeia (USP), European Pharmacopoeia (EP) and Chinese Pharmacopoeia (ChP), they are classified based on their possible risks to human health into one of the following three classes. A class 1 solvent refers to a solvent that is a human carcinogen and an environmental hazard, and its usage should be avoided. However, if using a class 1 solvent is unavoidable in order to produce a drug product with a significant therapeutic effect, its residue content in the drug product should be restricted to a limited amount, for example, benzene (2 ppm), carbon tetrachloride (4 ppm), 1,2-dichloroethane (5 ppm), 1,1-dichloroethene (8 ppm) and 1,1,1-trichloroethane (1500 ppm). A class 2 solvent refers to a solvent that is non-genotoxic but is an animal carcinogen. A class 2 solvent includes, but not limited to, acetonitrile (410 ppm), methylene chloride (600 ppm), toluene (890 ppm), methanol (3000 ppm), methyl cyclohexane (1180 ppm) and N-methylpyrrolidone (4840 ppm). A class 3 solvent refers to a solvent that has a low toxicity to human. Available data indicate that they are less toxic in acute or short-term studies and negative in genotoxicity studies. If there is no evidence otherwise, the residue of a class 3 solvent left in a drug product in an amount of less than 0.5% is acceptable. The class 3 solvent includes acetone.

In certain embodiments, the boiling point of the low boiling point and/or low toxicity solvent used in the acetylation reaction disclosed herein is less than 100° C., less than 90° C., less than 80° C., less than 70° C., or less than 60° C. In some embodiments, an oral median lethal dose (oral $LD_{50}$, rat) of the low boiling point and/or low toxicity solvent is higher than 1600 mg/Kg, higher than 2000 mg/Kg, higher than 2500 mg/Kg, higher than 3000 mg/Kg, higher than 3500 mg/Kg, higher than 4000 mg/Kg, higher than 4500 mg/Kg, higher than 5000 mg/Kg or higher than 5500 mg/Kg.

In some embodiments, the low boiling point and/or low toxicity solvent used in the acetylation reaction disclosed herein is dichloromethane, acetone or a combination thereof; or acetone, butanone or a combination thereof. In certain embodiments, when dichloromethane is employed in the acetylation reaction, it requires not only extraction and concentration, but also recrystallization with a different solvent. In other embodiments, when acetone, butanone or a combination thereof is employed in the acetylation reaction, prasugrel free base can be separated out in solid form directly without any work up procedures, such as extraction, concentration and recrystallization, which reduces the reaction time and energy consumption. Therefore, the method disclosed herein is suitable for industrial scale.

In certain embodiments, the solvent used herein is not Class 1 solvent or Class 2 solvent. In some embodiments, the solvent is not acetonitrile, dimethylformamide or toluene.

The acetylation reaction comprises acetylating the compound of formula (III) with an acetylation agent. Any acetylating agent that can be used for the acetylation reaction may be used herein. In certain embodiments, the acetylating agent is acetyl chloride, acetyl bromide, acetic anhydride or a combination thereof. In some embodiments, the acetylating agent is acetic anhydride.

In certain embodiments, the molar ratio of the compound of Formula (III) to acetic anhydride is from 1:1 to 1:5. In some embodiments, the molar ratio is from 1:1.1 to 1:1.5.

The acetylation reaction disclosed herein may be carried out in the present of a base. The base is not particularly limited. Any base, such as a primary amine, tertiary amine, secondary amine or a combination thereof, that can be used for the acetylation reaction may be used herein. In some embodiments, the base is a tertiary or secondary amine, such as triethylamine, tributylamine, diisopropylethylamine, diethylamine, dipropylamine, dibutylamine or a combination thereof; or diazabicyclo octane, diazabicyclo undecene or a combination thereof. In certain embodiments, the base is diethylamine or triethylamine. In certain embodiments, the molar ratio of compound of Formula (III) to the base is from 1:1 to 1:5. In some embodiments, the molar ratio is from 1:1.1 to 1:2.0.

The acetylation reaction disclosed herein may be carried out in the present of an acetylation catalyst. Any acetylation catalyst that can be used for the acetylation reaction may be used herein. In some embodiments, the acetylation catalyst is 4-dialkylaminopyridine, wherein the alkyl is $C_1$-$C_6$ alkyl. In certain embodiments, the acetylation catalyst is 4-dimethylaminopyridine, 4-diethylamino pyridine, 4-propylamino pyridine or a combination thereof. In some embodiments, the acetylation catalyst is 4-dimethylaminopyridine.

Any reaction temperature that can be used for the acetylation reaction may be used herein. In some embodiments, the reaction temperature is from about −10° C. to about 30° C. In certain embodiments, the reaction temperature is from about −5° C. to about 20° C., from about −5° C. to about 5° C., or from about −2° C. to about 2° C. In some embodiments, the temperature is about 0° C.

Any reaction time that can be used for the acetylation reaction may be used herein. In some embodiments, the reaction time is from 0.1 hours to 48 hours, from 0.5 hours to 24 hours, from 0.5 hours to 18 hours, or from 0.5 hours to 12 hours.

In some embodiments, the compound of Formula (III) is prepared by condensing a compound of Formula (IV) with a compound of Formula (V) or its salt thereof to form a condensation product; and purifying the condensation product,

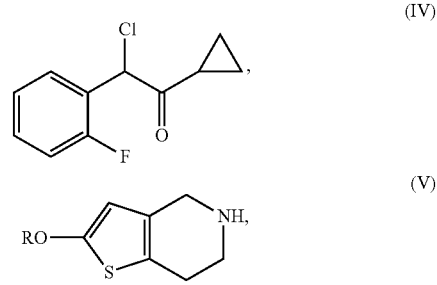

wherein R is a hydroxyl protecting group.

The compound of Formula (IV) used herein can be purchased from ZhuHai HaiRuiDe Biological Technology Co., Ltd. or from other commercial sources. The compound of Formula (V) could be prepared according to the method disclosed in PCT Patent Publication No. WO 1996/011203.

In certain embodiments, after the condensation reaction was completely, the crude product of the compound of Formula (III) is purified to improve its purity, and thus the purity of the final product prasugrel. In some embodiments, the crude product of the compound of Formula (III) is purified by recrystallizing from a solvent mixture of acetone and water.

In certain embodiments, the volume ratio of acetone to water in the solvent mixture is from 0.5:1 to 3:1. In certain embodiments, the volume ratio is from 0.8:1 to 2.5:1. In some embodiments, the volume ratio is from 0.9:1 to 2.1:1. In some embodiments, the volume ratio is from 0.9:1 to 1.1:1. In some embodiments, the volume ratio is from 1.9:1 to 2.1:1. In some embodiments, the volume ratio is 1:1. In some embodiments, the volume ratio is 2:1. In certain embodiments, the volume of acetone is from about 7 mL to about 10 mL per gram of the compound of Formula (V). In some embodiments, with regard to per gram of the compound of Formula (V), the volume of acetone is 8 mL.

In certain embodiments, the recrystallization of the compound of Formula (III) comprises dissolving the crude compound of Formula (III) in the solvent mixture of acetone and water to form a solution; cooling the solution to a temperature from about −5° C. to 10° C., stirring the solution for about 3 hours until crystals are formed; filtering and drying the crystals to obtain the compound of Formula (III).

In some embodiments, the molar ratio of the compound of Formula (V) or its salt thereof to the compound of Formula (IV) or its salt thereof is from 1:1 to 1:3. In certain embodiments, the molar ratio is from 1:1.0 to 1:1.5. In some embodiments, the molar ratio is from 1:1.1 to 1:1.2.

In certain embodiments, the condensation reaction disclosed herein is carried out in the presence of a base. The base is not particularly limited. Any base that can be used for the condensation reaction may be used herein. In some embodiments, the base is a primary amine, tertiary amine, secondary amine or a combination thereof. In some embodiments, the base is a tertiary or secondary amine, such as triethylamine, tributylamine, diisopropylethylamine, diethylamine, dipropylamine, dibutylamine, diazabicyclo octane, diazabicyclo undecene or tetramethylethylenediamine or a combination thereof. In certain embodiments, the base is triethylamine or diethylamine. In some embodiments, the molar ratio of the compound of Formula (V) to the base is from 1:1 to 1:2. In some embodiments, the molar ratio is from 1:1.1 to 1:1.3.

In some embodiments, the condensation reaction disclosed herein is carried out in the presence of an ammonium salt or a quaternary ammonium salt to promote the reaction.

In certain embodiments, the condensation reaction disclosed herein is carried out in the presence of an additive to catalyze the reaction. Any additive that can catalyze the condensation reaction may be used herein. In some embodiments, the additive is an alkali metal halide. In some embodiments, the alkali metal halide is an alkali metal bromide, such as lithium bromide, sodium bromide, potassium bromide, or cesium bromide or a combination thereof. In some embodiments, the alkali metal halide is an alkali metal iodide, such as lithium iodide, sodium iodide, potassium iodide or cesium iodide or a combination thereof. In certain embodiments, the additive is sodium bromide or sodium iodide or a combination thereof. In some embodiments, the molar ratio of compound of Formula (V) to the additive is from 1:0.005 to 1:0.05. In some embodiments, the molar ratio is 1:0.01.

The solvent used in the condensation reaction is not particularly limited. Any solvent that does not inhibit the condensation reaction and can dissolve the starting materials to some extent may be used herein. In some embodiments, the solvent includes an ether solvent, a halogenated solvent, an ester solvent, a ketone solvent, an aromatic solvent, or a combination thereof. In certain embodiments, the ether solvent is tetrahydrofuran, dioxane, methyl t-butyl ether, dimethoxyethane, diethylene glycol dimethyl ether, triethylene glycol dimethyl ether or a combination thereof. In some embodiments, the halogenated solvent is dichloromethane or 1,2-dichloroethane or a combination. In certain embodiments, the ester solvent is ethyl acetate, isopropyl acetate or a combination thereof. In some embodiments, the ketone solvent is acetone, methyl ethyl ketone or a combination thereof. In some embodiments, the aromatic hydrocarbon solvent is benzene, toluene or xylene or a combination thereof.

Any reaction temperature that can be used for the condensation reaction may be used herein. In certain embodiments, the reaction temperature is in from 0° C. to 40° C. In some embodiments, the reaction temperature is from 10° C. to 35° C. In some embodiments, the reaction temperature is room temperature.

The method for preparing prasugrel disclosed herein has many advantages, such as the starting materials and reagents are readily available and cheap; the problem about thermal instability of prasugrel is resolved; the loss of prasugrel is reduced; and the yield of prasugrel is increased. The yield of prasugrel is higher than 85% and the purity of prasugrel is higher than 99.5%. Therefore, the method disclosed herein can be used to prepare the pharmaceutically acceptable salts of prasugrel.

The prasugrel free base prepared by the method disclosed herein can be converted to pharmaceutically acceptable salts of prasugrel. The salts of prasugrel may be an inorganic acid salt, an organic acid salt or a combination thereof. In certain embodiments, the inorganic acid salt is hydrochloride or sulfate. In certain embodiments, the organic acid salt is an organic sulfonate, such as p-toluenesulfonate or methanesulfonate, or a carboxylic acid salt, such as acetate or propionate. In some embodiments, the inorganic acid salt is hydrochloride. In certain embodiments, the method for preparing prasugrel hydrochloride comprising dissolving prasugrel free base in a solvent to form a solution, and adding hydrochloric acid to the solution to obtain prasugrel hydrochloride. The hydrochloric acid can be added dropwise, or in one batch, two batches or more than two batches. In one embodiment, hydrochloric acid is added dropwise.

The solvent used in the method for preparing prasugrel hydrochloride is not particularly restricted. Any solvent that can dissolve the starting material to some extent and has no adverse effect on the reaction can be used herein. In some embodiments, the solvent is an aromatic hydrocarbon solvent, such as benzene, toluene or xylene; a halogenated solvent, such as dichloromethane, chloroform, carbon tetrachloride or 1,2-dichloroethane; an ether solvent, such as diethyl ether, diisopropyl ether, tetrahydrofuran or diethylene glycol dimethyl ether; a ketone solvent, such as acetone, methyl ethyl ketone or diethyl ketone; an ester solvent, such as ethyl acetate, isopropyl acetate or butyl acetate; a nitrile solvent, such as acetonitrile or propionitrile. In certain embodiments, the solvent is the ether solvent, the ketone solvent, the ester solvent, the nitrile solvent or a combination thereof. In some embodiments, the solvent is tetrahydrofuran, acetone, methyl ethyl ketone, ethyl acetate, acetonitrile or a combination thereof. In certain embodiments, the solvent is tetrahydrofuran, acetone or a combination thereof.

The reaction temperature for preparing prasugrel hydrochloride depends on the reagent, the solvent and the like. In certain embodiments, the reaction temperature is from -10° C. to 40° C. In some embodiments, the reaction temperature is from -5° C. to 20° C.

In a certain embodiments, the method for preparing prasugrel hydrochloride comprising adding prasugrel free base to an ether solvent or a ketone solvent to form a solution, stirring the solution at room temperature, adding hydrochloric acid dropwise to the solution for more than 1 hour, seeding the solution with prasugrel hydrochloride crystals, and cooling the resulting mixture to -5° C. to 10° C., which is then stirred for 15 hours, filtered and washed to obtain prasugrel hydrochloride.

Polymorph is an important physical and chemical property of a compound. For a drug existing in different crystalline forms, because of different crystal lattices, the crystalline forms may have different physical and chemical properties, such as melting point, solubility and stability. These properties not only affect processing and production of the drug, but also affect the stability, solubility and bioavailability of the drug. Therefore, the polymorphs of prasugrel hydrochloride affect the quality, safety and effectiveness of the drug, which renders it unsuitable in pharmaceutical applications. Therefore, this invention investigates the different crystallization behaviors of prasugrel hydrochloride and provides herein is a method of crystallizing prasugrel hydrochloride suitable for industrial production. Prasugrel hydrochloride prepared by the crystallization method provided herein is substantially pure. Also several novel crystalline forms of prasugrel hydrochloride under different crystallization conditions have been identified and found to be substantially pure. These new crystalline forms are designated as form H1, form H2 and form H3 in the following description.

As used herein, the term "substantially pure" refers to a purity of at least about 85%, or at least about 90%, or at least about 93%, or at least about 95%, or at least about 98%, or at least about 99%.

Figure 3:
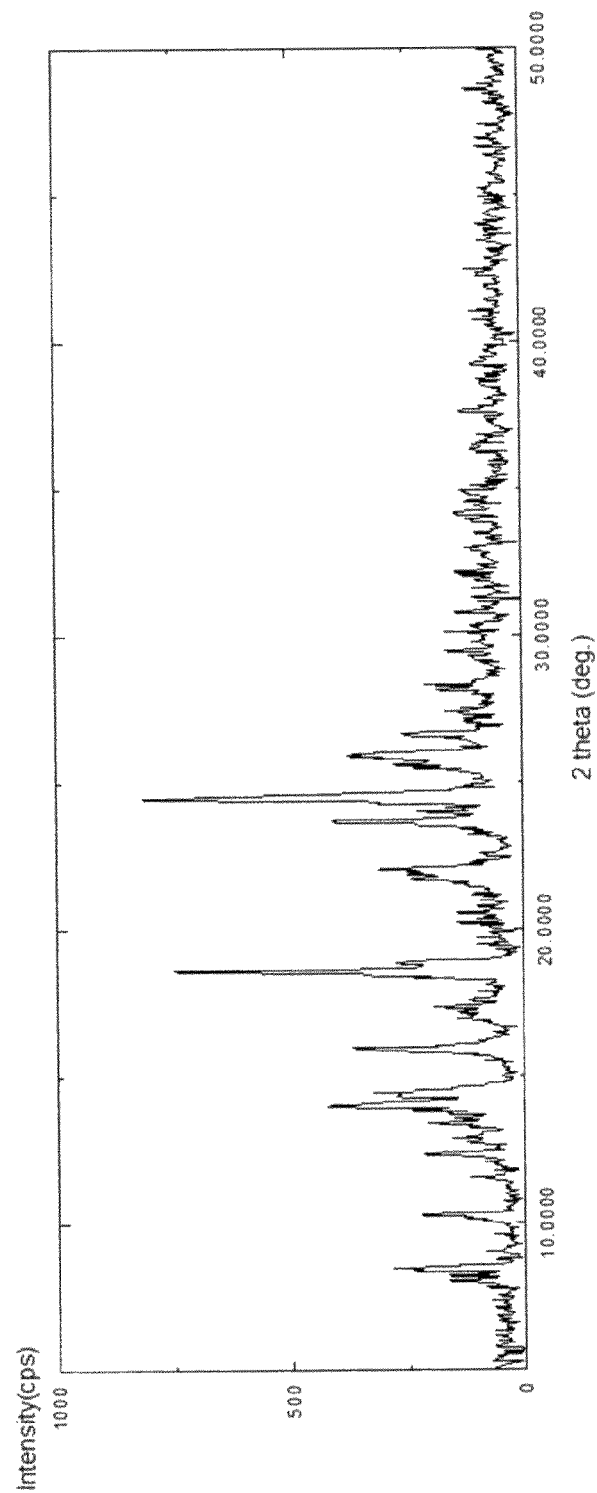
FIG. 3 depicts the X-ray powder diffractogram of the novel crystalline form H1 of prasugrel hydrochloride which was measured using CuK alpha radiation, wherein an ordinate or Y-axis is diffraction intensities in counts/second (cps) and an abscissa or X-axis is the diffraction angle two theta in degrees.

In certain embodiments, a substantially pure new crystalline form of prasugrel hydrochloride is the crystalline form H1 having the following physical properties:

its X-ray powder diffraction pattern (XRPD) comprises peaks expressed in degrees 2θ at 18.56 and 24.46 degrees;
its X-ray powder diffraction pattern (XRPD) comprises peaks expressed in degrees 2θ at 14.02, 15.92, 18.56, 23.66, 24.46, 25.92 and 26.62 degrees;
its X-ray powder diffraction pattern (XRPD) comprises peaks expressed in degrees 2θ at 8.02, 8.46, 10.28, 12.34, 12.88, 13.38, 14.02, 14.36, 15.92, 17.36, 18.56, 18.86, 20.54, 22.04, 23.66, 24.46, 25.92, 26.62, 28.3, 29.46 and 30.7 degrees; or
its X-ray powder diffraction pattern (XRPD) substantially as depicted in FIG. 3.

The crystalline form H1 can also be characterized by using other well-known analytical techniques, for example its melting point is from 153.6° C. to 160.2° C.

Figure 4:
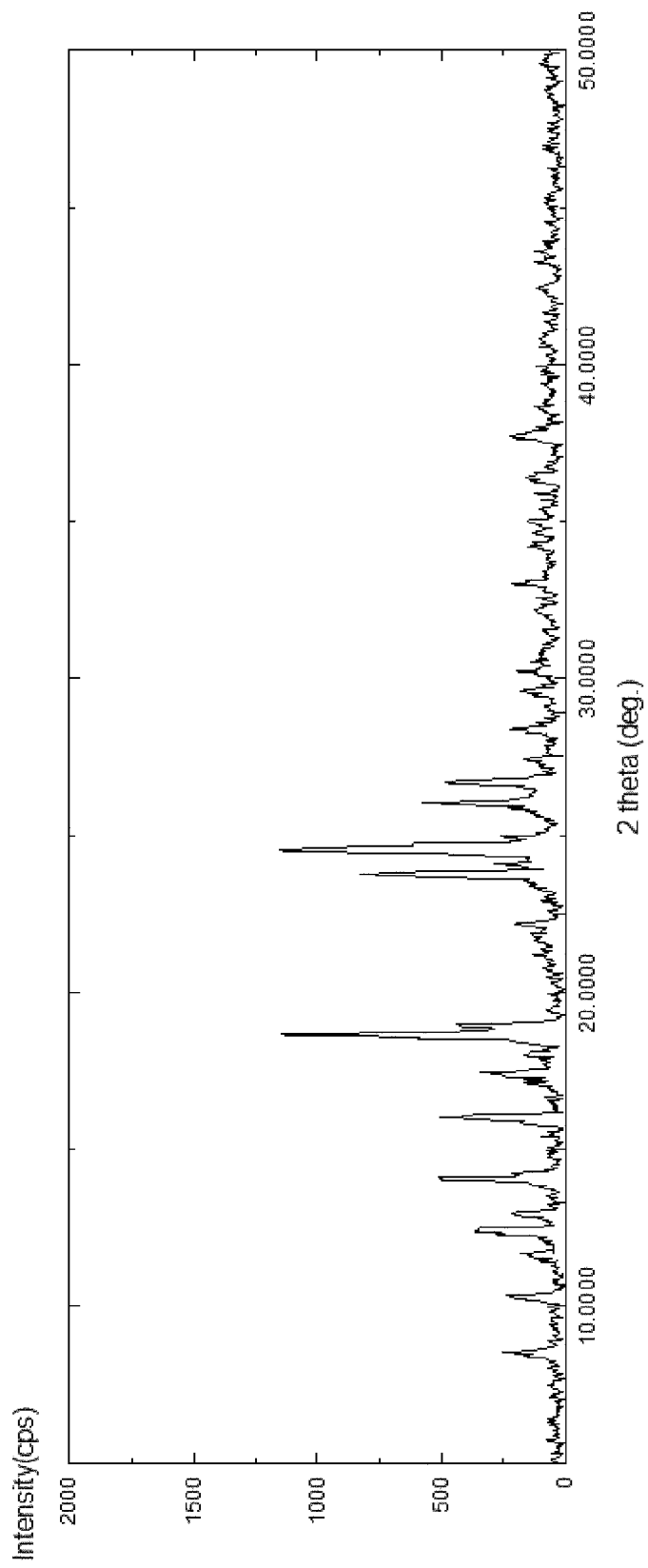
FIG. 4 depicts the X-ray powder diffractogram of the novel crystalline form H2 of prasugrel hydrochloride which was measured using CuK alpha radiation, wherein an ordinate or Y-axis is diffraction intensities in counts/second (cps) and an abscissa or X-axis is the diffraction angle two theta in degrees.

In some embodiments, a substantially pure new crystalline form of prasugrel hydrochloride is the crystalline form H2 having the following physical properties:
its X-ray powder diffraction pattern (XRPD) comprises peaks expressed in degrees 2θ at 18.00, 23.76 and 24.54 degrees;
its X-ray powder diffraction pattern (XRPD) comprises peaks expressed in degrees 2θ at 14.06, 16.00, 18.00, 23.76, 24.54, 26.0 and 26.7 degrees;
its X-ray powder diffraction pattern (XRPD) comprises peaks expressed in degrees 2θ at 8.54, 10.32, 11.66, 12.40, 12.94, 14.06, 16.00, 17.42, 18.00, 18.64, 18.94, 21.80, 22.16, 23.76, 24.54, 26.0, 26.7, 28.3, 29.6, 30.24 and 34.98 degrees; or
its X-ray powder diffraction pattern substantially as depicted in FIG. 4.

The crystalline form H2 can also be characterized by using other well-known analytical techniques, for example its melting point is from 133.7° C. to 139.5° C.

Figure 5:
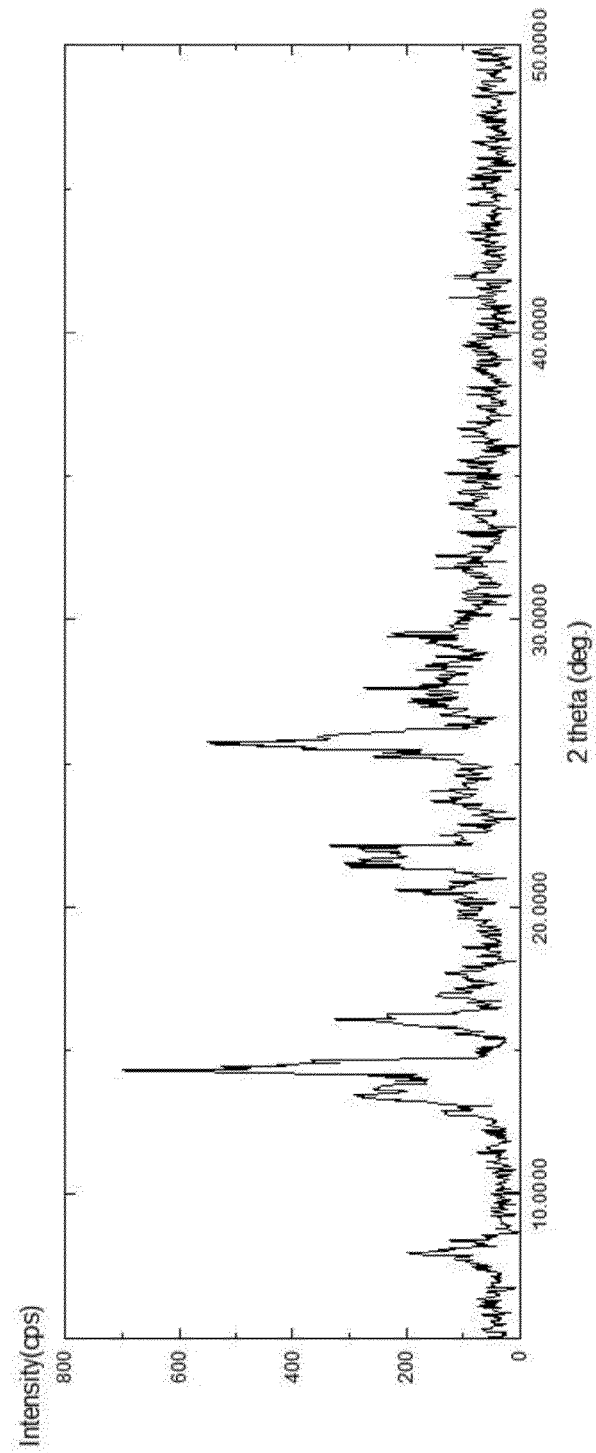
FIG. 5 depicts the X-ray powder diffractogram of the novel crystalline form H3 of prasugrel hydrochloride which was measured using CuK alpha radiation, wherein an ordinate or Y-axis is diffraction intensities in counts/second (cps) and an abscissa or X-axis is the diffraction angle two theta in degrees.

In certain embodiments, a substantially pure new crystalline form of prasugrel hydrochloride is the crystalline form H3 having the following physical properties:
its X-ray powder diffraction pattern (XRPD) comprises peaks expressed in degrees 2θ at 14.34 and 25.66 degrees;
its X-ray powder diffraction pattern (XRPD) comprises peaks expressed in degrees 2θ at 13.38, 13.78, 14.34, 16.06, 21.48, 22.06 and 25.66 degrees;
its X-ray powder diffraction pattern (XRPD) comprises peaks expressed in degrees 2θ at 7.98, 12.86, 13.38, 13.78, 14.34, 16.06, 17.12, 18.66, 20.52, 21.48, 22.06, 23.70, 25.66, 27.14, 27.64, 28.32 and 29.44 degrees; or
its X-ray powder diffraction pattern substantially as depicted in FIG. 5.

The crystalline form H3 can also be characterized by using other well-known analytical techniques, for example its melting point is from 162.1° C. to 166.9° C.

In certain embodiments, the new crystalline form of prasugrel hydrochloride is form H1, form H2 or form H3. In some embodiments, the new crystalline form of prasugrel hydrochloride is crystalline form H2 or form H3. In certain embodiments, the new crystalline form of prasugrel hydrochloride is crystalline form H2 or H3 and free of form H1. In some embodiments, the new crystalline form of prasugrel hydrochloride is form H2 and free of form H1 and form H3. In some embodiments, the new crystalline form of prasugrel hydrochloride is crystalline form H3 and free of form H1 and form H2.

The 2θ values of the X-ray powder diffraction peaks of the crystalline forms disclosed herein have experimental errors varying from one machine to another and from one sample to another. The 2θ values or peak amplitudes of the X-ray powder diffraction peaks may have slight differences. The experimental errors or numerical differences may be about ±degree, about ±0.8 degrees, about ±0.5 degrees, about ±0.3 degrees, about ±0.2 degrees, about ±0.1 degrees, about ±0.05 degrees, or about ±0.01 degrees. Therefore, the 2θ values or numerical values of peaks cannot be regarded as absolute.

The crystalline form H1, form H2 and form H3 of prasugrel hydrochloride disclosed herein have good properties and hence their high bioavailability based on the experimental results.

This invention provides a crystallization method for preparing prasugrel hydrochloride. The crystallization method disclosed herein can convert any crystalline forms of prasugrel hydrochloride to obtain substantially pure crystalline forms of prasugrel hydrochloride.

In certain embodiments, the crystallization method disclosed herein comprises dissolving prasugrel hydrochloride in a good solvent to form a solution and adding the prepared solution slowly into an anti-solvent to precipitate crystal.

In some embodiments, the good solvent is a polar solvent, wherein the polar solvent is an alcohol solvent or a carboxylic acid solvent. In certain embodiments, the alcohol solvent is methanol, ethanol, n-propanol, isopropanol or n-butanol or a combination thereof. In some embodiments, the alcohol solvent is methanol. In some embodiments, the carboxylic acid solvent is formic acid, acetic acid or benzoic acid or a combination thereof. In some embodiments, the carboxylic acid solvent is acetic acid.

In certain embodiments, the anti-solvent is a non-polar solvent, wherein the non-polar solvent is an ethereal solvent, an aromatic solvent, an ester solvent, a ketone solvent, a hydrocarbon solvent, or a combination thereof. In some embodiments, the ether solvent is tetrahydrofuran, diethyl ether, methyl t-butyl ether, dimethoxyethane, diethylene glycol dimethyl ether, triethylene glycol dimethyl ether or a combination thereof. In some embodiments, the aromatic solvent is benzene, toluene, xylene or a combination thereof. In some embodiments, the ester solvent is ethyl acetate, isopropyl acetate, n-butyl acetate, tert-butyl acetate or a combination thereof. In some embodiments, the ketone solvent is acetone, butanone, methyl ethyl ketone or a combination thereof. In some embodiments, the hydrocarbon solvent is n-hexane, cyclohexane, pentane or a combination thereof.

In certain embodiments, the volume of the good solvent is from 1.0 ml to 10.0 ml, from 1.0 ml to 7.0 ml, or from 2.0 ml to 4.0 ml with respect to 1 gram of prasugrel hydrochloride.

In some embodiments, the volume of the anti-solvent is from 10 ml to 50 ml, from 15 ml to 45 ml, from 20 ml to 40 ml, or from 25 ml to 35 ml with respect to 1 gram of prasugrel hydrochloride.

In certain embodiments, the crystallization method disclosed herein further comprises dissolving prasugrel hydrochloride in solvent promoted by stirring or ultrasound, and the like. The dissolving temperature is generally less than 60° C., less than 55° C., less than 50° C., less than 45° C., or less than 40° C. in the dissolving process.

In some embodiments, the crystallization method disclosed herein is carried out at a temperature from −10° C. to 40° C., or from −5° C. to 20° C.

The crystals may be isolated by any known collection methods such as by vacuum filtration, gravity filtration, or suction filtration after crystallization. The isolated crystal may carry mother liquor. The isolated crystals may be washed by a suitable solvent if necessary. In some embodiments, the isolated crystal is washed by an anti-solvent.

Figure 6:
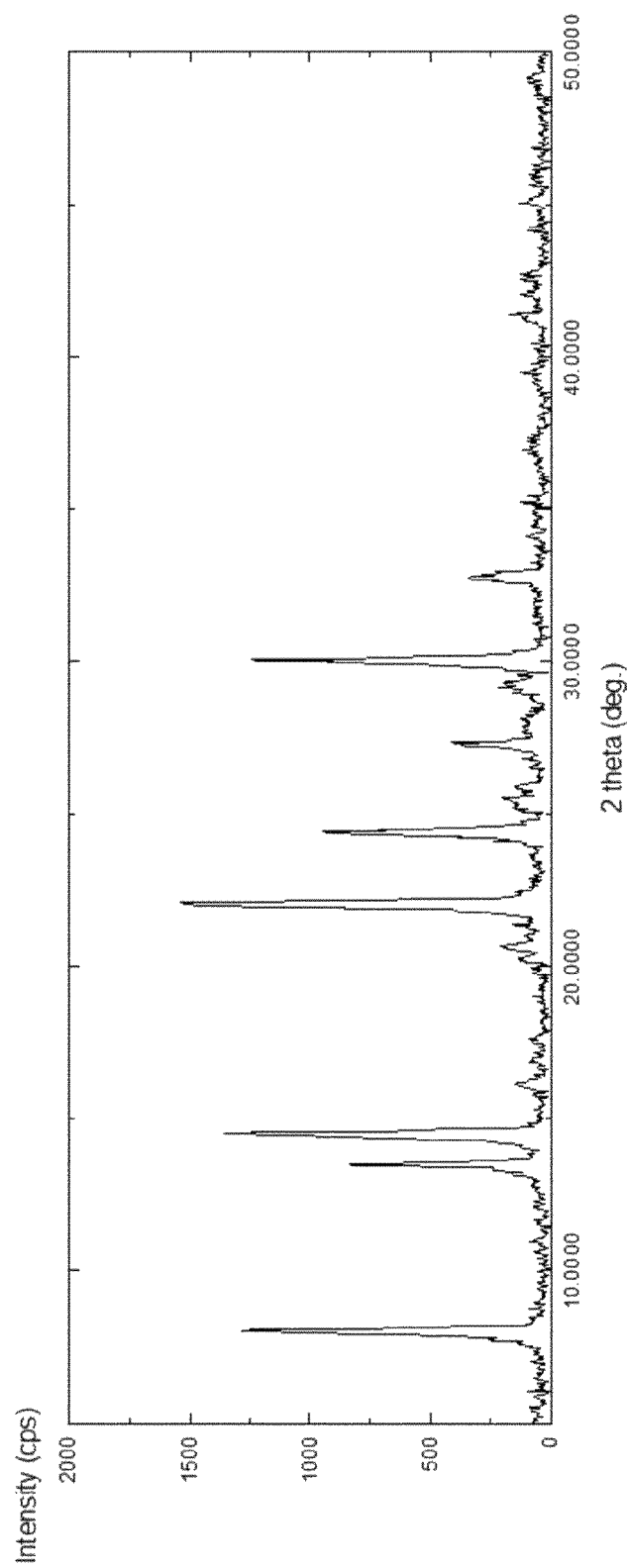
FIG. 6 depicts the X-ray powder diffractogram of the novel crystalline form B2 of prasugrel hydrochloride which was measured using CuK alpha radiation, wherein an ordinate or Y-axis is diffraction intensities in counts/second (cps) and an abscissa or X-axis is the diffraction angle two theta in degrees.

In certain embodiments, disclosed herein are the crystallization methods for preparing the crystalline form B2 of prasugrel hydrochloride with high purity, wherein the good solvent is an alcohol solvent and the anti-solvent is ethyl acetate, isopropyl acetate, n-butyl acetate or tert-butyl acetate, and the like. In some embodiments, the good solvent is methanol and the anti-solvent is ethyl acetate to provide the crystalline form B2 of prasugrel hydrochloride with high purity. Its X-ray powder diffraction pattern (XRPD) comprises peaks at about 8.08, 13.60, 14.58, 16.24, 20.78, 21.34, 22.12, 25.58, 25.96, 27.34 and 30.14 degrees in term of 2θ as depicted in FIG. 6.

In certain embodiments, the purity of the crystalline form B2 of prasugrel hydrochloride prepared by the crystallization methods disclosed herein is higher than 99%. In some embodiments, the purity is higher than 99.7%.

In some embodiments, the good solvent used in the crystallization methods is carboxylic acid solvent to provide prasugrel hydrochloride in crystalline form H1, form H2 or form H3.

In certain embodiments, disclosed herein is the crystallization method for preparing the crystalline form H1, wherein the good solvent is acetic acid and the anti-solvent is an ester solvent such as ethyl acetate, isopropyl acetate, n-butyl, tert-butyl acetate or a combination thereof or is an aromatic solvent such as benzene, toluene, xylene or a combination thereof or is ethyl acetate, toluene or a combination thereof.

In some embodiments, to provide the crystalline form H2, the good solvent used in the crystallization methods is acetic acid and the anti-solvent is hydrocarbon solvent, such as n-hexane, cyclohexane, pentane or a combination thereof or n-hexane.

In certain embodiments, to provide the crystalline form H3, the good solvent used in the crystallization methods is acetic acid, and the anti-solvent is ether solvent, such as tetrahydrofuran, diethyl ether, methyl t-butyl ether, dimethoxyethane, diethylene glycol dimethyl ether, triethylene glycol dimethyl ether or a combination thereof or methyl t-butyl ether.

This invention involves the selection of suitable solvents in the crystallization method disclosed herein and thus improves the yield of prasugrel hydrochloride. The yield of each step is higher than 85%. The single crystalline form of prasugrel hydrochloride prepared by the method disclosed herein is substantially pure. The synthetic process complies with the factory GMP production requirements and is industrially applicable.

The novel crystalline forms of prasugrel hydrochloride disclosed herein have excellent performance in oral absorbability, activating metabolism and inhibiting platelet aggregation and have low toxicity and good stability during processing and storage. Therefore, the novel crystalline forms of prasugrel hydrochloride disclosed herein can be used to prepare drugs for preventing or treating diseases caused by thrombosis or embolism. The novel crystalline forms of prasugrel hydrochloride disclosed herein can be used to prevent or treat diseases caused by thrombosis or embolism. Provided herein is a method of using the novel crystalline forms of prasugrel hydrochloride disclosed herein to prevent or treat diseases caused by thrombosis or embolism. This method includes administrating the novel crystalline forms of prasugrel hydrochloride disclosed herein to the patient suffering from those diseases.

The substantially pure crystalline forms of prasugrel hydrochloride can be further prepared into a variety of solid oral dosage forms. Some non-limiting examples of the solid dosage forms include capsules, tablets, pills, powders and granules. These dosage forms comprise the active ingredient and at least one pharmaceutical acceptable excipients or carriers. Some non-limiting examples of the excipients or carriers comprise sodium citrate, calcium phosphate, fillers, binders, moisturizers, disintegrants, retarders, absorption enhancers, wetting agents, absorbents, lubricants and a combination thereof. Some non-limiting examples of the fillers include starch, lactose, sucrose, glucose, mannitol, and silicic acid, or a combinations thereof. Some non-limiting examples of the binders include carboxymethylcellulose, alginates, gelatin, polyvinylpyrrolidone, sucrose, gum arabic and a combination thereof, wherein the moisturizers include glycerol. Some non-limiting examples of the disintegrants include agar-agar, calcium carbonate, potato starch or tapioca starch, alginic acid, certain silicates, sodium carbonate, low substituted hydroxypropyl cellulose and a combination thereof. Some non-limiting examples of the retarders include paraffin. Some non-limiting examples of the absorption enhancers include quaternary ammonium compounds. Some non-limiting examples of the wetting agents include cetyl alcohol, monostearic acid glyceride and a combination thereof. Some non-limiting examples of the absorbents include kaolin, bentonite and a combination thereof. Some non-limiting examples of the lubricants include talc, calcium stearate, magnesium stearate, solid polyethylene glycols, sodium lauryl sulfate and a combination thereof.

EXAMPLES

Disclosed herein is a method for preparing prasugrel and new crystalline forms of prasugrel hydrochloride. Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. Furthermore, numeric ranges are provided so that the range of values is recited in addition to the individual values within the recited range being specifically recited in the absence of the range.

In order to provide a better understanding of the present invention, examples of the present invention are described in detail below.

Example 1

Preparation of Prasugrel in Different Solvents 2-(Tert-butyldimethylsilyloxy)-5-(α-cyclopropylformyl-2-fluorobenzyl)-4,5,6,7-tetrahydrothieno[3,2-c]pyridine (3.0 g) was dissolved in the solvent described in Table 1 to form a solution and the solution was cooled to 0° C. Triethylamine (1.02 g) was then added followed by 4-dimethylaminopyridine (DMAP) (0.02 g). After the reaction mixture was stirred for 10 minutes at the same temperature, acetic anhydride (0.83 g) was added to the solution. The reaction was monitored by Thin Layer Chromatography (TLC) (petroleum ether/ethyl acetate=10/1 or 5/1) until the reaction was completed. After the reaction was completed, cold water was added to the reaction mixture and the mixture was stirred for 15 minutes. It was then cooled to −5° C. and further stirred for 3 hours before collecting the crystal as prasugrel free base. Solid precipitate was collected. The yield of prasugrel was calculated and the results were shown in Table 1.

TABLE 1

Comparison of the yields of prasugrel prepared in different solvents.

| No. | Reaction solvent | Solvent volume | Reaction temperature | Reaction Time | Yield |
|---|---|---|---|---|---|
| A | $CH_2Cl_2$ | 15 mL | 0° C. | 15 h | 88.7% |
| B | $CH_2Cl_2$ | 15 mL | 25° C. | 12 h | 79.49% |
| C | toluene | 15 mL | 0° C. | 12 h | 69.63% |
| D | acetone | 15 mL | 25° C. | 2 h | 86.87% |
| E | THF | 15 mL | 0° C. | 4 h | 63.09% |
| F | acetonitrile | 15 mL | 0° C. | 1 h | 81.26% |
| G | acetone | 15 mL | 0° C. | 1 h | 71.23% |
| H | Ethyl acetate | 15 mL | 0° C. | 15 h | 76.71% |
| I | butanone | 15 mL | 0° C. | 12 h | 82.18% |

As shown in Table 1, when the low boiling point and/or low toxicity solvent such as acetone or dichloromethane is used as the solvent in the acetylation reaction, the yield of prasugrel is comparatively higher. Among many low boiling point and/or low toxicity solvents, when acetone or dichloromethane used as the solvent can lead to a higher prasugrel yield compared to other solvents. In addition, acetone and dichloromethane have relatively low toxicity.

Example 2

The Method for Preparing 2-(tert-butyldimethylsilyloxy)-5-(α-cyclopropyl formyl-2-fluorobenzyl)-4,5,6,7-tetrahydrothieno[3,2-c]pyridine (Compound of Formula III)

5,6,7,7a-Tetrahydro-4H-thieno[3,2-c]pyridin-2-one (2.0 g) was added to dichloromethane (10 mL) and stirred for 10 minutes to form a solution at 25° C. followed by dropwise addition of triethylamine (1.22 g) to the solution. After the reaction mixture was stirred for 15 minutes, a solution of tert-butyldimethylsilyl chloride (1.81 g) in dichloromethane was added to the reaction mixture at the same temperature. The reaction mixture was stirred at 25° C. until the reaction was completed which was monitored by Thin Layer Chromatography (TLC) (methanol/ethyl acetate=3/7). Triethylamine (2.12 g), sodium iodide (0.02 g) and 2-bromo-2-(2-fluorophenyl)-1-cyclopropylethanone (2.96 g) were then added to the mixture stirred at 25° C. and the reaction was monitored by Thin Layer Chromatography (TLC) (methanol/ethyl acetate=3/7). After the reaction was completed, the organic phase was washed with phosphate buffer (pH 6-7) and concentrated under reduced pressure at 30° C. to obtain 2-(tert-butyldimethylsilyloxy)-5-(α-cyclopropylformyl-2-fluorobenzyl)-4,5,6,7-tetrahydrothieno[3,2-c]pyridine as a crude product. The crude product (1 g) was dissolved in acetone/water (2:1 v/v, acetone volume=8 ml) and the mixture was kept at −5° C. for 3 hours for the crystallization method. The crystals were collected by filtration and dried in vacuum at 50° C. for 24 hours to obtain (tert-butyldimethylsilyloxy)-5-(α-cyclopropylformyl-2-fluorobenzyl)-4,5,6,7-tetrahydrothieno[3,2-c]pyridine having the HPLC purity of 99%. The yield was 85%.

Example 3

The Method for Preparing Prasugrel 2-(Tert-butyldimethylsilyloxy)-5-(α-cyclopropylformyl-2-fluorobenzyl)-4,5,6,7-tetrahydro-thieno[3,2-c]pyridine (3.0 g) prepared by example 2 was dissolved in acetone (10.0 mL) and the solution was cooled to 0° C. Triethylamine (1.02 g) was then added dropwise followed by adding 4-dimethylaminopyridine (DMAP) (0.025 g) and the mixture was stirred for 10 minutes at the same temperature. Acetic anhydride (0.83 g) in acetone was then added and the reaction was monitored by Thin Layer Chromatography (TLC) (petroleum ether/ethyl acetate=10/1 or 5/1). After the reaction was completed, cold water (7.5 mL) was then added to the reaction mixture. After the reaction mixture was stirred for 15 minutes, the reaction mixture was cooled to −5° C. and further stirred for 3 hours. Solid precipitate was collected by filtration followed by washing with a mixture of pre-cooled acetone/water (1:1 v/v) (10 ml). The obtained prasugrel free base was dried under vacuum at 50° C. for 24 hours. The yield was 85%.

Example 4

The Method for Preparing 2-(tert-butyldimethylsilyloxy)-5-(α-cyclopropyl formyl-2-fluorobenzyl)-4,5,6,7-tetrahydro-thieno[3,2-c]pyridine (Compound of Formula III)

5,6,7,7a-Tetrahydro-4H-thieno[3,2-c]pyridin-2-one (2.0 g) was added to dichloromethane (10 mL) and stirred for 10 minutes at 10° C. Triethylamine (1.22 g) was then added and the mixture was stirred for 15 minutes to form a reaction mixture. Tert-butyldimethylsilyl chloride (1.81 g) dissolved in dichloromethane was added to the mixture at 10° C. The mixture was stirred at 10° C. and the reaction was monitored by Thin Layer Chromatography (TLC) (methanol/ethyl acetate=3/7) until the reaction was completed. Triethylamine (2.12 g), sodium iodide (0.02 g) and 2-bromo-2-(2-fluorophenyl)-1-cyclopropyl-ethanone (1.5 molar eq.) were added slowly to the reaction mixture at 10° C. The reaction mixture was stirred at 25° C. and the reaction was monitored by Thin Layer Chromatography (TLC) (methanol/ethyl acetate=3/7). After the reaction was completed, the organic phase was then washed with phosphate buffer (pH 6-7), and concentrated under reduced pressure at 30° C. to obtain 2-(tert-butyldimethylsilyloxy)-5-(α-cyclopropylformyl-2-fluorobenzyl)-4,5,6,7-tetrahydrothieno[3,2-c]pyridine as a crude product. The crude product (1 g) was recrystallized using acetone/water (1:1 v/v) (acetone volume=10 ml) at −5° C. for 3 hours for the crystallization method. Crystal precipitate was collected by filtration and dried under vacuum at 50° C. for 24 hours to obtain (tert-butyldimethylsilyloxy)-5-(α-cyclopropylformyl-2-fluorobenzyl)-4,5,6,7-tetrahydro-thieno[3,2-c]pyridine with the HPLC purity of 96%. The yield was 90%.

Example 5

The Method for Preparing Prasugrel 2-(Tert-butyldimethylsilyloxy)-5-(α-cyclopropylformyl-2-fluorobenzyl)-4,5,6,7-tetrahydro-thieno[3,2-c]pyridine (1.0 eq.) prepared by example 4 was dissolved in acetone (10.0 mL) and the mixture was cooled to 0° C. Triethylamine (1.1 eq.) was added slowly followed by adding 4-dimethylaminopyridine (DMAP) (0.025 g) and the mixture was stirred for 10 minutes. Acetic anhydride (1.5 eq.) in acetone was then added. The reaction was monitored by Thin Layer Chromatography (TLC) (petroleum ether/ethyl acetate=10/1 or 5/1). After the reaction was completed, cold water (7.5 mL) was added to the reaction mixture and the mixture was stirred for 15 minutes. It was then cooled to −5° C. and further stirred for 3 hours. After filtration, solid precipitate was washed with a mixture of pre-cooled acetone/water (1:1 v/v) (10 ml). The obtained prasugrel free base was dried under vacuum at 50° C. for 24 hours. The yield was 90%.

Example 6

Determining the Purity of Prasugrel

The purity of prasugrel prepared according to example 3 and example 5 was determined. The conditions are shown below.

Instrument: Agilent RRLC 1200; DAD detector; Agilent ZORBAX StableBond SB-C18 4.6×250 mm, 5 μm column
Mobile phase: $CH_3CN$, $H_2O$
Wavelength: 254 nm
Injection volume: 1 uL Prasugrel prepared by example 3 and example 5 was determined by HPLC, the results are as shown in Tables 1 and 2.

TABLE 1

The HPLC Results of Prasugrel Prepared According to Example 3.

| Retention time (min.) | Peak area | Area (%) | Peak height |
|---|---|---|---|
| 13.57 | 4826 | 0.04 | 669 |
| 14.62 | 11482100 | 99.74 | 1412411 |
| 15.94 | 4596 | 0.04 | 401 |
| 16.95 | 9023 | 0.08 | 1184 |
| 17.39 | 7046 | 0.06 | 703 |
| 24.04 | 4333 | 0.04 | 543 |
| Totals | 11511929 | 100.00 | 1415911 |

TABLE 2

The HPLC Results of Prasugrel Prepared By Example 5.

| Retention time (min.) | Peak area | Area (%) | Peak height |
|---|---|---|---|
| 14.62 | 6395825 | 99.97 | 785819 |
| 16.95 | 2042 | 0.03 | 310 |
| Totals | 6397867 | 100.00 | 786129 |

According to Table 1 and Table 2, the overall purity of prasugrel prepared according to examples 3 and 5 disclosed herein is higher than 99.5%.

Example 7

The Method for Preparing Prasugrel Hydrochloride

Prasugrel free base prepared by example 3 (2.0 g) disclosed herein was dissolved in acetone (25 ml) with stirring at 20° C. until complete dissolution and the mixture was further stirred for 10 minutes. A solution of hydrochloric acid in acetone (0.46 ml hydrochloric acid (37 wt. %) dissolved in 5 ml acetone) was added slowly to the reaction mixture over 1 hour at 20° C. After the addition, a seed crystal (0.05 g) (crystalline form B2 of prasugrel hydrochloride), the resulting mixture was stirred at 20° C. for 15 hours followed by filtration. The obtained crystal was washed with acetone and dried under vacuum at 50° C. for 24 hours. The resulting product was prasugrel hydrochloride crystalline Form B2 with the HPLC purity of 99.74%. The yield was 90%.

Example 8

The Method for Preparing Crystalline Form A of Prasugrel Hydrochloride

Prasugrel free base prepared by example 3 (2.3 g) disclosed herein was dissolved in tetrahydrofuran (30 ml) with stirring at room temperature until complete dissolution and the resulting mixture was further stirred for 10 minutes. A solution of hydrochloric acid in tetrahydrofuran (0.53 ml hydrochloric acid (37 wt. %) dissolved in 5 ml tetrahydrofuran) was added slowly to the resulting mixture over 1 hour at room temperature. The mixture was stirred at −5° C. for 15 hours followed by filtration. The obtained crystal was washed with tetrahydrofuran and dried under vacuum at 50° C. for 24 hours. The resulting product was prasugrel hydrochloride crystalline Form A. The yield was 98%.

Example 9

The Method for Preparing Crystalline Form B2 of Prasugrel Hydrochloride

Methanol (200 ml) was added to the product prepared by example 7 or example 8 (100 g) disclosed herein with stirring at 25-35° C. to form a solution. The solution was filtered to obtain a mother liquor. The mother liquor was added slowly to ethyl acetate (3000 ml) (a seed crystal (2% w/w) of prasugrel hydrochloride crystalline form B2 was added before the addition of prasugrel hydrochloride in methanol). The resulting mixture was stirred at 10° C. for 15 hours followed by filtration. The resulting crystals was washed with ethyl acetate (300 ml) and dried under vacuum at 50° C. for 24 hours. The resulting product was prasugrel hydrochloride crystalline form B2 with the HPLC purity of 99.87%. The yield was 85-88%.

Example 10

The Method for Preparing Crystalline Form H1 of Prasugrel Hydrochloride

Acetic acid (10 ml) was added to the product prepared by example 7 (2 g) with stirring at a temperature below 45° C. to form a solution. The solution was filtered to obtain a mother liquor. The mother liquor was added slowly to ethyl acetate (60 ml). After the addition, the resulting mixture was stirred at 15-20° C. for 15 hours followed by filtration. The resulting crystals was washed with ethyl acetate (10 ml) and dried under vacuum at 50° C. for 24 hours. The resulting product was prasugrel hydrochloride crystalline form H1. The yield was 90%.

Example 11

The Method for Preparing Crystalline Form H1 of Prasugrel Hydrochloride

Acetic acid (10 ml) was added to the product prepared by example 8 (2 g) with stirring at a temperature below 45° C. to form a solution. The solution was filtered to obtain a mother liquor. The mother liquor was added slowly to toluene (60 ml). The resulting mixture was stirred at 15-20° C. for 15 hours followed by filtration. The resulting crystals was washed with toluene (10 ml) and dried under vacuum at 50°

C. for 24 hours. The resulting product was prasugrel hydrochloride crystalline form H1. The yield was 93.5%.

Example 12

The Method for Preparing Crystalline Form H2 of Prasugrel Hydrochloride

Acetic acid (10 ml) was added to the product prepared by example 7 (2 g) with stirring at a temperature below 45° C. to form a solution The solution was filtered to obtain a mother liquor. The mother liquor was added slowly to n-hexane (60 ml). After the addition, the resulting mixture was stirred at 15-20° C. for 15 hours followed by filtration. The resulting crystals was washed with n-hexane (10 ml) and dried under vacuum at 50° C. for 24 hours. The resulting product was prasugrel hydrochloride crystalline form H2. The yield was 90.5%. The melting point was from 133.7° C. to 139.5° C.

Example 13

The Method for Preparing Crystalline Form H3 of Prasugrel Hydrochloride

Acetic acid (10 ml) was added to the product prepared by example 8 (2 g) with stirring at a temperature below 45° C. to form a solution. The solution was filtered to obtain a mother liquor. The mother liquor was added slowly to methyl tert-butyl ether (60 ml). The resulting mixture was stirred at 15-20° C. for 15 hours followed by filtration. The resulting crystals was washed with methyl tert-butyl ether (10 ml) and dried under vacuum at 50° C. for 24 hours. The resulting product was prasugrel hydrochloride crystalline form H3. The yield was 90.0%. The melting point was from 162.1° C. to 166.9° C.

Example 14

Solubility Test

According to the solubility test described in "Chinese Pharmacopoeia 2010", Topic and Requirement 15, the grinded sample in powder form was added to a certain amount of solvent at 25±2° C. The solution was strongly shaken for 30 seconds each time at 5 minute intervals to observe the solubility in a total testing time of 30 minutes. The solid was deemed as dissolved when no solid was detected in the mixture by human eyes. The solubility data are shown in Table 3.

TABLE 3

The Solubility of Crystalline Forms In 0.1M HCl

| Crystalline sample | Solvent | Sample weight (mg) | Solvent volume (mL) | Solubility (mg/mL) |
|---|---|---|---|---|
| Form B2 | 0.1M HCl | 300 | 7.5 | 40 |
| Form H1 | 0.1M HCl | 300 | 6 | 50 |
| Form H2 | 0.1M HCl | 300 | 6 | 50 |
| Form H3 | 0.1M HCl | 300 | 6 | 50 |

According to the results, the crystalline forms H1, form H2 and form H3 of prasugrel hydrochloride disclosed herein have good properties and good bioavailability.

Those illustrative embodiments herein are used to help understand the methods and core ideas about this present invention. It should be noted that many adaptations and modifications may be made thereto without departing from the scope of the appended claims in accordance with the common general knowledge of those of ordinary skill in the art.

What is claimed is:

1. A crystalline form of prasugrel hydrochloride, wherein the crystalline form is form H1 having an X-ray powder diffraction pattern comprising peaks expressed in degrees 2θ at 14.02, 15.92, 18.56, 23.66, 24.46, 25.92 and 26.62±0.3 degrees.

2. The crystalline form of claim 1, wherein the crystalline form is form H1 having an X-ray powder diffraction pattern comprising peaks expressed in degrees 2θ at 8.02, 8.46, 10.28, 12.34, 12.88, 13.38, 14.02, 14.36, 15.92, 17.36, 18.56, 18.86, 20.54, 22.04, 23.66, 24.46, 25.92, 26.62, 28.3, 29.46 and 30.7±0.3 degrees.

3. A method for preparing the crystalline form of prasugrel hydrochloride of claim 1 comprising dissolving prasugrel hydrochloride in a good solvent to form a solution; and forming crystals by adding the solution slowly into an anti-solvent, wherein the good solvent is an alcohol solvent, a carboxylic acid solvent or a combination thereof, and the anti-solvent is an ether solvent, an aromatic solvent, an ester solvent or a combination thereof.

4. The method of claim 3, wherein the good solvent is an alcohol solvent, or methanol, ethanol, n-propanol, isopropanol or n-butanol or a combination thereof, and the anti-solvent is an ester solvent or ethyl acetate.

5. The method of claim 3, wherein the good solvent is acetic acid, and the anti-solvent is an ester solvent or ethyl acetate.

6. A method for preventing or treating diseases caused by thrombosis or embolism in a patient by administering to the patient a pharmaceutically effective amount of the crystalline form of prasugrel hydrochloride of claim 1.

7. A crystalline form of prasugrel hydrochloride, wherein the crystalline form is form H3 having an X-ray powder diffraction pattern comprising peaks expressed in degrees 2θ at 13.38, 13.78, 14.34, 16.06, 21.48, 22.06 and 25.66±0.3 degrees.

8. The crystalline form of claim 7, wherein the crystalline form has an X-ray powder diffraction pattern comprising peaks expressed in degrees 2θ at 7.98, 12.86, 13.38, 13.78, 14.34, 16.06, 17.12, 18.66, 20.52, 21.48, 22.06, 23.70, 25.66, 27.14, 27.64, 28.32 and 29.44±0.3 degrees.

9. A method for preparing the crystalline form of prasugrel hydrochloride of claim 7 comprising dissolving prasugrel hydrochloride in a good solvent to form a solution; and forming crystals by adding the solution slowly into an anti-solvent, wherein the good solvent is an alcohol solvent, a carboxylic acid solvent or a combination thereof, and the anti-solvent is an ether solvent, an aromatic solvent, an ester solvent or a combination thereof.

10. The method of claim 9, wherein the good solvent is an alcohol solvent, or methanol, ethanol, n-propanol, isopropanol or n-butanol or a combination thereof, and the anti-solvent is an ester solvent or ethyl acetate.

11. The method of claim 9, wherein the good solvent is acetic acid, and the anti-solvent is an ether solvent or methyl tert-butyl ether.

12. A method for preventing or treating diseases caused by thrombosis or embolism in a patient by administering to the patient a pharmaceutically effective amount of the crystalline form of prasugrel hydrochloride of claim 7.

* * * * *